United States Patent
Özbek et al.

(10) Patent No.: US 11,227,441 B2
(45) Date of Patent: Jan. 18, 2022

(54) TECHNIQUE FOR CALIBRATING A REGISTRATION OF AN AUGMENTED REALITY DEVICE

(71) Applicant: Scopis GmbH, Berlin (DE)

(72) Inventors: Christopher Özbek, Berlin (DE); Marc Käseberg, Biesenthal (DE); Markus Kastrop, Berlin (DE); Christian Winne, Berlin (DE)

(73) Assignee: Scopis GmbH, Berlin (DE)

( * ) Notice: Subject to any disclaimer, the term of this patent is extended or adjusted under 35 U.S.C. 154(b) by 0 days.

(21) Appl. No.: 16/912,850

(22) Filed: Jun. 26, 2020

(65) Prior Publication Data
US 2021/0005020 A1 Jan. 7, 2021

(30) Foreign Application Priority Data

Jul. 4, 2019 (EP) .................................... 19184370

(51) Int. Cl.
*G06T 19/00* (2011.01)
*G06T 7/80* (2017.01)
(Continued)

(52) U.S. Cl.
CPC ........ *G06T 19/003* (2013.01); *G02B 27/0093* (2013.01); *G02B 27/0172* (2013.01);
(Continued)

(58) Field of Classification Search
CPC ......... G06T 19/003; G06T 7/80; G06T 7/344; G02B 27/0093; G02B 27/0172
See application file for complete search history.

(56) References Cited

U.S. PATENT DOCUMENTS 6,433,760 B1 * 8/2002 Vaissie .................. G01S 17/875
345/8
6,753,828 B2 6/2004 Tuceryan et al.
(Continued)

FOREIGN PATENT DOCUMENTS

EP 3241088 A1 11/2017
EP 3117263 B1 5/2018
(Continued)

OTHER PUBLICATIONS

English language abstract and machine-assisted English translation for WO 2018/212437 extracted from espacenet.com database on Jul. 23, 2020, 20 pages.
(Continued)

*Primary Examiner* — Sarah Lhymn
(74) *Attorney, Agent, or Firm* — Howard & Howard Attorneys PLLC

(57) ABSTRACT

A method of calibrating a registration of an augmented reality device 2 comprised in a surgical navigation system 100 is provided. The method comprises obtaining a first transformation 38 between a coordinate system 40 of the augmented reality device 2 and a reference coordinate system 42 of the surgical navigation system 100, a second transformation 44 between a coordinate system of a reference object 24 and the reference coordinate system 42 and obtaining geometrical properties of the reference object 24. The method further comprises determining a visual representation 34 of the reference object 24 to be displayed by the augmented reality device 2 and obtaining at least one first viewing direction 56 of a user using the augmented reality device 2, the at least one first viewing direction 56 being associated with the reference coordinate system 42. The method comprises determining a calibrated first transformation, which is a transformation between the coordinate
(Continued)

system 40 of the augmented reality device 2 and the reference coordinate system 42.

20 Claims, 4 Drawing Sheets

(51) Int. Cl.
*G06T 7/33* (2017.01)
*G02B 27/00* (2006.01)
*G02B 27/01* (2006.01)
*G06T 7/00* (2017.01)

(52) U.S. Cl.
CPC ............ *G06T 7/0012* (2013.01); *G06T 7/344* (2017.01); *G06T 7/80* (2017.01); *G02B 2027/0138* (2013.01); *G06T 2207/30204* (2013.01)

(56) References Cited

U.S. PATENT DOCUMENTS

| | | | |
|---|---|---|---|
| 7,369,101 | B2 | 5/2008 | Sauer et al. |
| 9,906,778 | B2 | 2/2018 | Yamamoto |
| 10,192,361 | B2 | 1/2019 | Li et al. |
| 10,242,504 | B2 | 3/2019 | Li et al. |
| 2013/0258353 | A1* | 10/2013 | Kosmecki ............ G01B 21/042 356/616 |
| 2014/0168056 | A1* | 6/2014 | Swaminathan ......... G06F 3/147 345/156 |
| 2015/0103096 | A1 | 4/2015 | Gotoda |
| 2015/0288944 | A1* | 10/2015 | Nistico .................. G06T 15/20 345/156 |
| 2016/0225191 | A1 | 8/2016 | Mullins |
| 2016/0343164 | A1* | 11/2016 | Urbach .............. G02B 27/0093 |
| 2018/0018791 | A1 | 1/2018 | Guoyi |
| 2018/0116732 | A1 | 5/2018 | Lin et al. |
| 2018/0124387 | A1 | 5/2018 | Zhao et al. |
| 2018/0130227 | A1 | 5/2018 | Sato et al. |
| 2018/0185100 | A1 | 7/2018 | Weinstein et al. |
| 2018/0300551 | A1* | 10/2018 | Luccin ............... H04N 5/23293 |
| 2018/0303377 | A1* | 10/2018 | West .................... G06K 9/3216 |
| 2020/0275988 | A1* | 9/2020 | Johnson ................. A61B 90/39 |

FOREIGN PATENT DOCUMENTS

| | | |
|---|---|---|
| EP | 3321885 A1 | 5/2018 |
| WO | 2004113991 A2 | 12/2004 |
| WO | 2013128612 A1 | 9/2013 |
| WO | 2013179425 A1 | 12/2013 |
| WO | 2013179427 A1 | 12/2013 |
| WO | 2014128748 A1 | 8/2014 |
| WO | 2015103623 A1 | 7/2015 |
| WO | 2015139005 A1 | 9/2015 |
| WO | 2016109127 A1 | 7/2016 |
| WO | 2016126672 A1 | 8/2016 |
| WO | 2017192996 A2 | 11/2017 |
| WO | 2018129234 A1 | 7/2018 |
| WO | 2018203304 A1 | 11/2018 |
| WO | 2018212437 A1 | 11/2018 |
| WO | 2019004565 A1 | 1/2019 |

OTHER PUBLICATIONS

English language abstract and machine-assisted English translation for WO 2013/128612 extracted from espacenet.com database on Jul. 23, 2020, 17 pages.
English language abstract for WO 2014/128748 extracted from espacenet.com database on Jul. 23, 2020, 2 pages.
English language abstract for WO 2013/179425 extracted from espacenet.com database on Jul. 23, 2020, 2 pages.
English language abstract for WO 2013/179427 extracted from espacenet.com database on Jul. 23, 2020, 2 pages.
English language abstract and machine-assisted English translation for WO 2019/004565 extracted from espacenet.com database on Jul. 23, 2020, 19 pages.

\* cited by examiner

TECHNIQUE FOR CALIBRATING A REGISTRATION OF AN AUGMENTED REALITY DEVICE

CROSS-REFERENCE TO RELATED APPLICATIONS

This application claims priority to European Patent Application No. EP19184370.5, filed on Jul. 4, 2019, the entire contents of which are hereby incorporated by reference.

TECHNICAL FIELD

The present disclosure generally relates to an augmented reality device. It specifically relates to a method of calibrating a registration of an augmented reality device comprised in a surgical navigation system, an apparatus for calibrating a registration of an augmented reality device comprised in a surgical navigation system, and a computer program.

BACKGROUND

In the field of surgical navigation, augmented reality devices are beginning to be used in order to display relevant information to a user such as a surgeon. For example, a treatment is planned before surgery using two- or three-dimensional patient image data. Immediately before or during surgery, relevant data of the planned treatment such as an intended resection volume of body tissue or an intended placement of a screw into a bone can be shown to the surgeon via the augmented reality device.

Most commonly, head-mounted augmented reality devices are used to enable a free movement of the hands of the user. Such a head-mounted augmented reality device for surgical navigation is disclosed in US 2018/0185100 A1.

Some known augmented reality devices comprise an internal localization system which enables determining a position and orientation of the augmented reality device in a coordinate system of the augmented reality device. The accuracy of the internal localization system of the augmented reality devices is often insufficient for the surgical requirements at hand.

Usually, high accuracy localization systems are used in surgical navigation in order to determine the position and orientation of surgical instruments and body parts of a patient. To this end, tracking devices can be attached to surgical instruments and body parts to be tracked. The localization system may then detect the optical tracking devices and determine the position and orientation thereof. Such high accuracy localization systems enable a more precise determination of the position and orientation of a tracked object compared with the internal localization system of an augmented reality device.

In order to improve the accuracy of the internal localization system of an augmented reality device, it makes sense to combine the augmented reality device with a surgical navigation system which uses a high accuracy localization system to achieve gold standard accuracies. To combine the position determined by the augmented reality device in its coordinate system with positions determined by the localization system in a coordinate system of the surgical navigation system, a mechanism is required that joins both to a common frame of reference. One way to achieve this is to provide the augmented reality device with a tracking device which can be tracked by the high accuracy localization system comprised in the surgical navigation system.

A low quality tracking of the augmented reality device will result in incorrect transformation of coordinates of the localization system of the surgical navigation system into the coordinate system of the augmented reality device. This in turn will lead to visualizations in the augmented reality device that are not accurately overlaid for example on relevant anatomical parts of the patient.

Since the surgeon might want to rely on the accuracy of the augmented reality overlay to perform surgical tasks, several problems need to be solved. Firstly, it has to be considered how the surgeon can verify that the overlaid visualization is accurate. Secondly, it has to be considered how the surgeon can correct the overlaid visualization in case a deviation is detected.

SUMMARY

It is an object of the present disclosure to provide a solution which enables enhancing accuracy of an existing registration of an augmented reality device.

According to a first aspect, a method of calibrating a registration of an augmented reality device comprised in a surgical navigation system is provided. The method comprises obtaining first registration data describing a first transformation between a coordinate system of the augmented reality device and a reference coordinate system of the surgical navigation system. The method further comprises obtaining second registration data describing a second transformation between a coordinate system of a reference object and the reference coordinate system of the surgical navigation system. In addition, the method comprises obtaining reference object data describing geometric properties of the reference object and determining visualization data based on the first registration data, the second registration data and the reference object data, the visualization data describing a visual representation of the reference object to be displayed by the augmented reality device. The method further comprises obtaining viewing direction data describing at least one first viewing direction of a user using the augmented reality device, the at least one first viewing direction being associated with the reference coordinate system of the surgical navigation system, and determining calibrated first registration data based on the first registration data and the viewing direction data, the calibrated first registration data describing a calibrated transformation between the coordinate system of the augmented reality device and the reference coordinate system.

The at least one first viewing direction is for example associated with the reference coordinate system by being described in the reference coordinate system or by being transformable into the reference coordinate system, for example based on at least the first registration data. The at least one first viewing direction may be associated with the reference coordinate system by having a known spatial relationship with the reference coordinate system. This relationship may be determined based on at least one of the first registration data and other known or determinable transformations.

The augmented reality device may be configured as a head-mounted display (HMD). At least one of the first transformation, the second transformation and the calibrated transformation may be described by rotational and translational components, for example in the form of a matrix.

The coordinate system of the augmented reality device corresponds to an internal world coordinate system of the augmented reality device. At least one of a position and an orientation of the augmented reality device can be determined in the coordinate system of the augmented reality device by an internal tracking system comprised in the augmented reality device. For example, the internal tracking system is configured to determine the position and orientation of the augmented reality device in the internal world coordinate system. In one variant, the internal tracking system comprises at least one optical sensor such as a camera and optionally at least one distance sensor such as an infrared sensor.

The reference coordinate system of the surgical navigation system may correspond to a tracking coordinate system of the navigation system. At least one of a position and orientation of a tracked object can be determined in the reference coordinate system based on a tracking by the surgical navigation system. For example, the surgical navigation system comprises an optical or electromagnetic tracking system configured to track an object. The surgical navigation system may further comprise a localization system. The localization system comprised in the surgical navigation system may be configured to determine a position and orientation of the tracked object in the reference coordinate system, for example based on the tracking by the localization system. The localization system may further be configured to determine at least one of the first registration data and the second registration data. An optical tracking system may comprise at least one optical sensor such as a camera or a stereo camera. An electromagnetic tracking system may comprise a field generator and one or more field detection coils.

The coordinate system of the reference object is for example associated with a position and orientation of an optical, electromagnetic or any other tracking device. In one variant, the reference object has a known spatial relationship to the tracking device. In another variant, the reference object is the tracking device and comprises at least one marker. The reference object may include markers detectable by the tracking system comprised in the surgical navigation system. In one variant, at least two of the markers are indistinguishable from one another by the tracking system. The markers may be passive or active optical markers if an optical tracking system is used.

In one variant, the reference object comprises a body having predetermined geometric properties. At least one marker may be attached to the body. The predetermined geometric properties may comprise an indication of a relative position of at least two markers, which are attached to the body, to one another and/or to a given position on the body. The reference object data describes geometric properties of the reference object, for example the aforementioned predetermined geometric properties. The geometric properties may further comprise a three-dimensional model of the reference object, for example of the tracker body. The geometric properties may comprise at least one of an indication of an outline and an indication of a surface of the reference object.

The visualization data may describe a visual representation of the reference object depending on the at least one first viewing direction of the user. That is, the step of obtaining viewing direction data may be performed before the step of determining the visualization data. The step of determining the visualization data may comprise determining, based on the viewing direction data and the second registration data, a viewing direction of the user with respect to the reference object. This viewing direction may correspond to the at least one first viewing direction. The step of determining the visualization data may further comprise determining the visual representation of the reference object from this viewing direction based on the reference object data. The visual representation of the reference object to be displayed by the augmented reality device is determined such that it is to be displayed overlaid with the reference object. In other words, the visual representation of the reference object may describe a virtual reference object which is to be overlaid with the reference object by displaying it with the augmented reality device. For example, the visual representation of the reference object is to be displayed such that it appears to lie at the same position as the reference object. The position at which the visual representation is to be displayed may correspond to the position at which the virtual reference object for the user appears to lie in case the visual representation is displayed. In other words, the position at which the visual representation is to be displayed may not be a position on a display but a virtual position defining, i.e., the size and orientation of the visual representation.

The viewing direction data may be obtained by determining at least one of a position and orientation of the augmented reality device. The position and orientation may be associated with the reference coordinate system. The position and orientation is for example associated with the reference coordinate system by being described in the reference coordinate system. For example, a tracking device comprising at least one tracking marker is attached to the augmented reality device. The position and orientation of the augmented reality device may then be determined based on a tracking of the at least one tracking marker. In this case, a known relative position between the augmented reality device and the tracking device attached to the augmented reality device can be taken into account when determining the position and orientation of the augmented reality device in the reference coordinate system based on the tracking.

Alternatively, the position and orientation of the augmented reality device may be associated with the reference coordinate system by being transformable into the reference coordinate system, for example based on at least the first registration data. For example, the internal tracking system is configured to determine the position and orientation of the augmented reality device in the coordinate system of the augmented reality device. The position and orientation in the coordinate system of the augmented reality device may then be transformed into a position and orientation in the reference coordinate system by applying the transformation described by the first transformation data. In other words, the position and orientation of the augmented reality device may be associated with the reference coordinate system by having a known spatial relationship with the reference coordinate system. This relationship may be determined based on at least one of the first registration data and other known or determinable transformations.

The at least one first viewing direction may be described by at least one ray and/or line. For example, each first viewing direction is described by a line. In another variant, each first viewing direction is described by more than one line. For example, a first viewing direction may be described by a line representing a line of sight of an eye of the user using the augmented reality device.

The first viewing direction may be described by a plurality of lines representing different lines of sight of the eyes of the user. The viewing direction data may comprise additional information based on which the visualization data is determined. For example, the viewing direction data comprises information about a field of view of the user, a distance between the eye of the user and a display of the augmented reality device or else. The viewing direction data may describe several lines or rays having a common intersection point. For example, the intersection point corresponds to a focus point of the user. The intersection point may correspond to a look-at position associated with the reference coordinate system. For example, the intersection of two lines may be approximated to obtain the look-at position.

As mentioned above, the at least one first viewing direction is associated with the reference coordinate system. In more detail, the at least one ray and/or line describing the at least one first viewing direction is associated with the reference coordinate system. The at least one ray and/or line is associated with the reference coordinate system by being described in the reference coordinate system or by being transformable into the reference coordinate system, for example based on at least the first registration data. The at least one ray and/or line may be associated with the reference coordinate system by having a known spatial relationship with the reference coordinate system. This relationship may be determined based on at least one of the first registration data and other known or determinable transformations.

The viewing direction data may describe a plurality of first viewing directions, for example viewing directions which differ from one another due to movement of the augmented reality device with respect to the reference coordinate system. In one variant, a plurality of first viewing directions is described by the viewing direction data which describe a plurality of viewing directions of the user to a reference point, for example (i.e., a part of) the reference object. The plurality of first viewing directions may be used to determine a look-at position or a focus point of the user. Known optimization algorithms may be used in order to determine a point which best matches all or most of the first viewing directions. The look-at position and/or the focus point may be described by the viewing direction data.

For example, the step of determining calibrated first registration data comprises determining an internal transformation between a position at which the visual representation of the reference object is to be displayed and the at least one first viewing direction. For example, the internal transformation describes a rotational transformation between the position and the at least one first viewing direction. The rotational transformation may be determined by rotationally shifting the position onto a line describing the first viewing direction. In this case, the rotating may be performed around a rotation point, wherein the rotation point is defined by a position of the augmented reality, for example by a reference point of the augmented reality device. The rotation point may be defined by a position of an eye of the user. For example, the internal transformation describes a transformation between the position at which the visual representation is to be displayed and the focus point or the look-at point described by the viewing direction data or determined based on the at least one first viewing direction.

The step of determining calibrated registration data may comprise applying the internal transformation to the first transformation. Alternatively, it may comprise applying the first transformation to the internal transformation. For example, the internal transformation and the first transformation are described by matrices comprising rotational and translational components. The calibrated registration data may be determined by calculating a product of these matrices.

In one example, the method further comprises a step of obtaining trigger data. The trigger data for example describes a trigger signal to execute at least one of the obtaining of the first registration data, the obtaining of the second registration data, the determining of the visualization data, the obtaining of the viewing direction data and the determining of the calibrated first registration data. In one variant, the trigger data is determined based on a user interaction. The trigger data may be determined based on input of a user using the augmented reality device. The input of the user is for example one of a voice command, a user gesture and an input via a user interface such as a keyboard, a touchscreen, a mouse, a joystick or else. For example, the trigger data is determined based on a viewing direction (i.e., the first viewing direction) of a user using the augmented reality device. In one variant, the viewing direction of the user is determined and compared with a reference viewing direction. For example, in case the determined viewing direction of the user corresponds to the reference viewing direction within a given tolerance limit the trigger data describing the trigger signal is determined. In one example, the trigger data describing the trigger signal is determined in case the determined viewing direction of the user corresponds to a position of a part of the reference object. In other words, it may be determined that the user is looking at the reference object and as a result the trigger data may be determined. The determining of the trigger data may be part of the obtaining of the trigger data.

The method in one example further comprises a step of obtaining selection data describing a selection of a part of the reference object. The selection data may be determined based on a selection of the user. The selection of the user is for example one of a voice command, a user gesture and an input via a user interface such as a keyboard, a touchscreen, a mouse, a joystick or else. For example, the selection data is determined based on at least one second viewing direction of a user using the augmented reality device.

The step of obtaining selection data for example comprises obtaining selection viewing direction data describing at least one second viewing direction of the user. The at least one second viewing direction is for example associated with the reference coordinate system by being described in the reference coordinate system or by being transformable into the reference coordinate system, for example based on at least the first registration data. The at least one second viewing direction may be associated with the reference coordinate system by having a known spatial relationship with the reference coordinate system. This relationship may be determined based on at least one of the first registration data and other known or determinable transformations.

In one variant, the second viewing direction of the user is obtained or determined and compared with a reference viewing direction. For example, in case the obtained second viewing direction of the user corresponds to the reference viewing direction within a given tolerance limit, an object, for example a part of the reference object, which lies in the reference viewing direction is selected and this selection is described by the selection data.

In one example, it is determined that the second viewing direction of the user corresponds to a position of a part of the reference object. In other words, it may be determined that the user is looking at a certain part of the reference object and as a result this part may be selected and the selection data may be determined describing the selection of this part. That is, the method may comprise determining the selection of the part of the reference object by determining a part of the reference object which part's visual representation is to be displayed by the augmented reality device at a position corresponding to the at least one second viewing direction described by the selection viewing direction data.

The second viewing direction may be described by at least one ray and/or line. The second viewing direction is for example described by plurality of lines representing different lines of sight of the eyes of the user. The selection viewing direction data may comprise additional information based on which the visualization data is determined. For example, the selection viewing direction data comprises information about a field of view of the user, a distance between the eye of the user and a display of the augmented reality device or else. The selection viewing direction data may describe several lines or rays having a common intersection point. For example, the intersection point corresponds to a focus point of the user. The intersection point may correspond to a look-at position associated with the reference coordinate system. For example, the intersection of two lines may be approximated to obtain the look-at position.

As mentioned above, the at least one second viewing direction is associated with the reference coordinate system. In more detail, the at least one ray and/or line describing the at least one second viewing direction is associated with the reference coordinate system. The at least one ray and/or line is associated with the reference coordinate system by being described in the reference coordinate system or by being transformable into the reference coordinate system, for example based on at least the first registration data. The at least one ray and/or line may be associated with the reference coordinate system by having a known spatial relationship with the reference coordinate system. This relationship may be determined based on at least one of the first registration data and other known or determinable transformations.

The selection viewing direction data may describe a plurality of second viewing directions, for example viewing directions which differ from one another due to movement of the augmented reality device with respect to the reference coordinate system. In one variant, a plurality of second viewing directions is described by the selection viewing direction data which describe a plurality of viewing directions of the user to a reference point, for example (i.e., a part of) the reference object. The plurality of second viewing directions may be used to determine a look-at position or a focus point of the user. To this end, known optimization algorithms may be used in order to determine a point which best matches all or most of the second viewing directions. The look-at position and/or the focus point may be described by the selection viewing direction data.

At least one of the step of obtaining viewing direction data and the step of obtaining selection viewing direction data for example comprises obtaining at least one position and/or orientation of the augmented reality device. The at least one position and/or orientation of the augmented reality device may be associated with the reference coordinate system. The at least one position and/or orientation of the augmented reality device may be described in the reference coordinate system. In one variant, the at least one position and/or orientation of the augmented reality device is transformable into the reference coordinate system based on at least one known or determinable transformation. For example, the position and orientation of the augmented reality device is described by the position and orientation of a reference point of the augmented reality device. The position of the augmented reality device can be used as the rotation point to determine the calibrated first registration data. For example, the reference point of the augmented reality device can be used as the rotation point.

At least one of the step of obtaining viewing direction data and the step of obtaining selection viewing direction data may comprise obtaining at least one position and/or orientation of at least a part of an eye of the user using the augmented reality device. The position and/or orientation of the at least a part of the eye of the user may be associated with the reference coordinate system. Also in this case, the term "associated with the reference coordinate system" comprises the case that the position and/or orientation of the at least a part of the eye of the user is described in the reference coordinate system and the case that the position and/or orientation of the at least a part of the eye of the user is transformable into the reference coordinate system, for example based on at least one known or determinable transformation. A position of the eye of the user can be determined and used as the rotation point to determine the calibrated first registration data.

According to a second aspect, an apparatus for calibrating a registration of an augmented reality device comprised in a surgical navigation system is provided. The apparatus is configured to obtain first registration data describing a first transformation between a coordinate system of the augmented reality device and a reference coordinate system of the surgical navigation system. The apparatus is further configured to obtain second registration data describing a second transformation between a coordinate system of a reference object and the reference coordinate system of the surgical navigation system. In addition, the apparatus is configured to obtain reference object data describing geometric properties of the reference object and to determine visualization data based on the first registration data, the second registration data and the reference object data, the visualization data describing a visual representation of the reference object to be displayed by the augmented reality device. The apparatus is further configured to obtain viewing direction data describing at least one first viewing direction of a user using the augmented reality device, the at least one first viewing direction being associated with the reference coordinate system of the surgical navigation system, and to determine calibrated first registration data based on the first registration data and the viewing direction data, the calibrated first registration data describing a calibrated transformation between the coordinate system of the augmented reality device and the reference coordinate system. The apparatus may be configured to execute the method described herein.

According to a third aspect, a surgical navigation system is provided. The surgical navigation system is for example the surgical navigation system described above with reference to the first aspect. In one variant, the surgical navigation system comprises the apparatus and at least one of the augmented reality device and a localization system configured to determine the first registration data and/or the second registration data. For example, the localization system is the localization system described above. The localization system may comprise an optical tracking system configured to detect an optical marker, for example an optical marker attached to the reference object.

According to a fourth aspect, a computer program is provided. The computer program comprises instructions which, when the program is running on a processor, cause the processor to perform the method steps of the method described herein. The processor may be comprised in the surgical navigation system.

According to a fifth aspect, a program storage medium is provided on which the program described herein is stored. The program storage medium may be comprised in the surgical navigation system.

According to a sixth aspect, a data stream is provided. The data stream carries information which represents the program described herein. The data stream may be transmitted to the surgical navigation system. The data stream is for example transmitted over a network such as the internet or over an internal network of a hospital.

BRIEF DESCRIPTION OF THE DRAWINGS

In the following, several embodiments of the present disclosure are described with reference to the figures, wherein.

DETAILED DESCRIPTION

Figure 1:
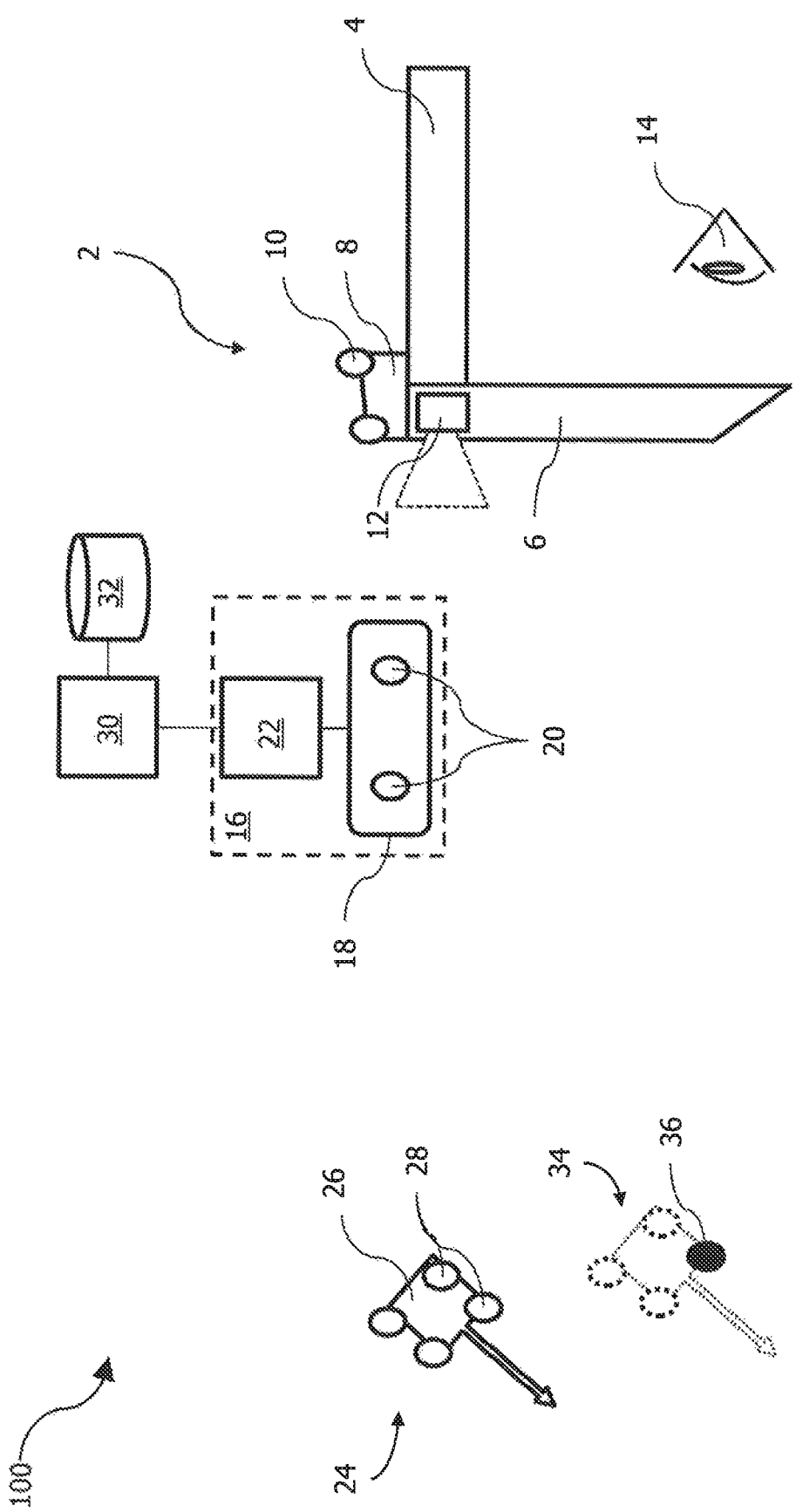
FIG. 1 shows an embodiment of a surgical navigation system comprising an augmented reality device.

In the following description, for purposes of explanation and not limitation, specific details are set forth in order to provide a thorough understanding of the present disclosure. It will be apparent to one skilled in the art that the present disclosure may be practiced in other embodiments that depart from these specific details. Those skilled in the art will further appreciate that the steps, services and functions explained herein may be implemented using individual hardware circuitry, using software functioning in conjunction with a programmed microprocessor or general purpose computer, using one or more Application Specific Integrated Circuits (ASICs) and/or using one or more Digital Signal Processors (DSPs). It will also be appreciated that when the present disclosure is described in terms of a method, it may also be embodied in one or more processors and one or more memories coupled to the one or more processors, wherein the one or more memories store one or more programs that perform the steps, services and functions disclosed herein when executed by the one or more processors. That is, a computer program is provided comprising instructions which, when the program is running on a processor, cause the processor to perform the method described herein. In addition, a program storage medium on which the program is stored is provided. Also, a data stream carrying information which represents the program described herein is provided.

In the following description of exemplary embodiments, the same reference numerals denote the same or similar components.

FIG. 1 shows an embodiment of a surgical navigation system 100. The surgical navigation system 100 comprises an augmented reality device 2. The augmented reality device 2 comprises a body 4 and a display system 6 attached to the body 4. Also attached to the body 4 is an optical tracking device 8 comprising at least one optical marker 10. It is noted that instead of the optical tracking device 8 and the optical marker 10, other types of tracking devices and markers can be used. In the following, it is nevertheless referred to optical tracking devices, optical markers and an optical tracking system. The augmented reality device 2 further comprises an internal tracking system 12. The internal tracking system 12 may further comprise an optical sensor such as an infrared sensor, a laser sensor or a camera. In the shown example, the augmented reality device 2 is a head-mounted augmented reality device which is positioned such that an eye 14 of a user wearing the augmented reality device 2 is positioned behind the display systems 6. An image can be displayed on the display system 6 such that the user is able to see the image with the eye 14.

The surgical navigation system 100 further comprises a localization system 16. The localization system 16 is able to determine the position and orientation of the augmented reality device 2 by tracking the at least one optical marker 10 by an optical tracking system 18. The optical tracking system 18 comprises at least one optical sensor. In this example, the optical tracking system 18 comprises two cameras 20 that provide three-dimensional image data. The localization system in the shown example also comprises a processor 22 connected to the optical tracking system 18 and configured to determine the position and orientation of the augmented reality device 2. The localization system 16 may be further configured to determine at least one of first registration data and second registration data. Registration data generally describes a transformation between two coordinate systems which remains constant during surgery. Several different methods are known of registering a coordinate system of a tracking system with a coordinate system of three-dimensional image data of a patient. A position and orientation of surgical instruments can be tracked in the coordinate system of the tracking system and transformed into the coordinate system of the three-dimensional image data based on the registration to enable real-time surgical navigation. Whilst the time-dependent position and orientation can be described by a time-dependent transformation in the coordinate system of the tracking system, the transformation between the two coordinate systems in most cases remains constant.

Also shown in FIG. 1 is a reference object 24. The reference object 24 comprises a body 26 with attached optical markers 28. The localization system 16 is configured to track the reference object 24. The processor 22 is configured to determine the position and orientation of the reference object 24 based on positions of the optical markers 28 detected by the optical tracking system 18. As noted above, in case another type of marker, such as an electromagnetic marker, is used, the tracking system 18 may be a tracking system of another type, for example an electromagnetic tracking system.

A processor 30 of the surgical navigation system 100 is configured to obtain the first registration data, obtain the second registration data, obtain reference object data, determine visualization data, obtain viewing direction data, obtain selection viewing direction data, obtain trigger data, and determine calibrated first registration data.

For example, one or more of the data may be obtained from a data storage 32 by processor 30. The processor 30 may be further configured to perform the steps described above with respect to processor 22. In this case, processor 22 may not be provided.

A visual representation 34 of the reference object 24 is described by the visualization data and displayed by the augmented reality device 2 via display system 6 to the user. A part 36 of the reference object 24 is highlighted in the visual representation 34, for example an optical marker. The visual representation 34 is to be displayed in an overlaid manner with the reference object 24. In the shown configuration, the visual representation 34 is displayed with an offset to reference object 24. The reason for this offset will be described with reference to FIG. 2 in more detail.

Figure 2:
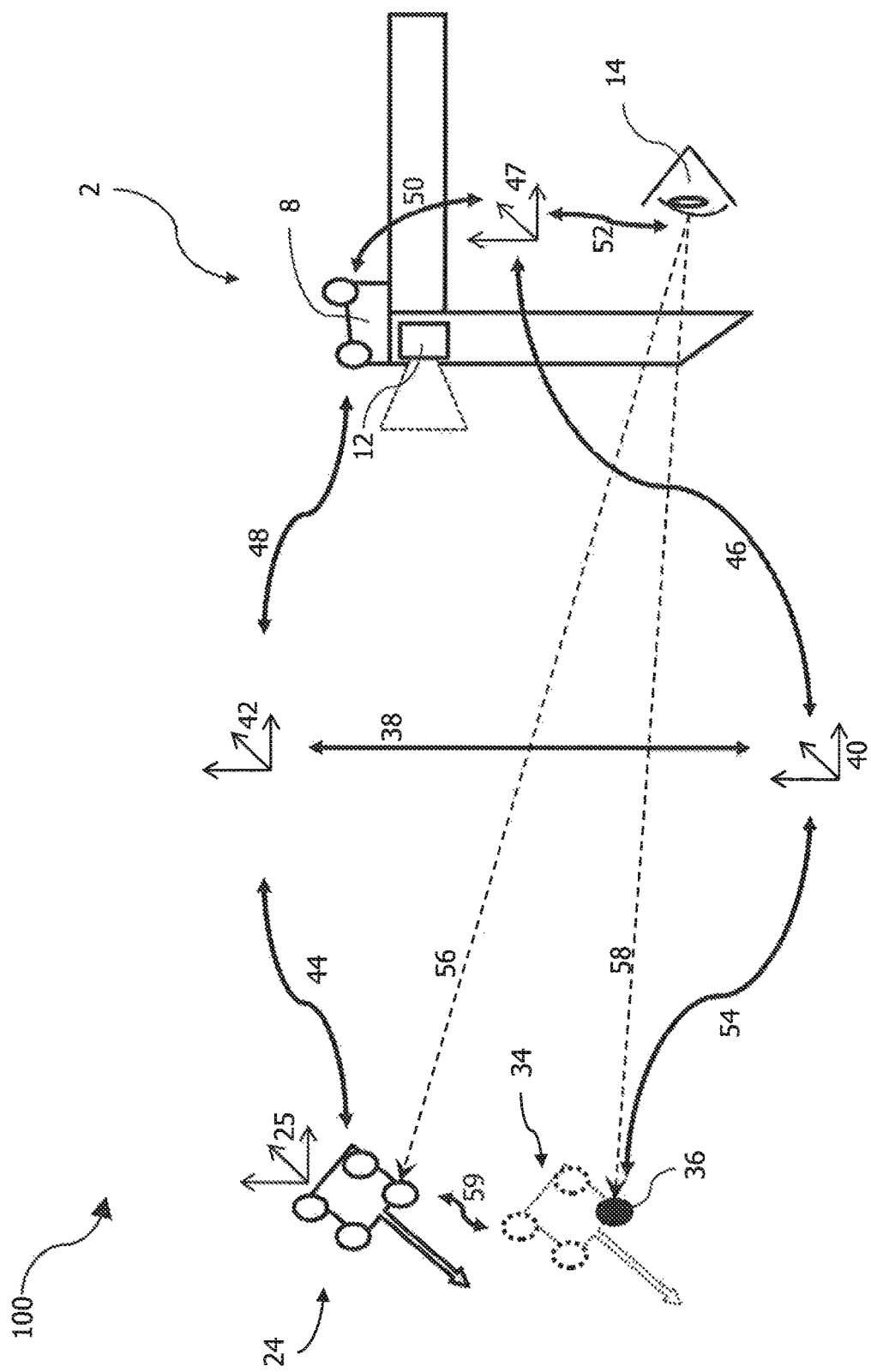
FIG. 2 shows an embodiment of a surgical navigation system and transformations between individual components thereof.

FIG. 2 shows an embodiment of the surgical navigation system 100 of FIG. 1. The first registration data describes a first transformation 38 between a coordinate system 40 of the augmented reality device 2 and a reference coordinate system 42 of the surgical navigation system 100. The second registration data describes a second transformation 44 between the reference object 24 and the reference coordinate system 42. A position and orientation of the augmented reality device 2 in the coordinate system 40 of the augmented reality device 2 can be determined by the internal tracking system 12. For example, one or more sensors comprised in the internal tracking system 12 are used in order to monitor the surroundings of the augmented reality device 2 so as to determine a change in position and orientation of the augmented reality device with respect to the surroundings. The position and orientation of the augmented reality device 2 in the coordinate system 40 of the augmented reality device 2 can be described by a third transformation 46. In the shown embodiment, the third transformation 46 describes a transformation between the coordinate system 40 of the augmented reality device and a location coordinate system 47 which is defined by a reference point of the augmented reality device 2. For example, the reference point is chosen such that it corresponds to a predetermined, intended position of the eye 14 of the user. As can be seen in FIG. 2, in some cases the eye 14 of the user lies at a different position. This offset may be compensated with the calibration method and the surgical navigation system 100 described herein.

A position and orientation of the augmented reality device 2 in the reference coordinate system 42 can be determined in two different ways. Firstly, the position and orientation of the augmented reality device 2 in the reference coordinate system 42 can be determined by tracking the optical tracking device 8 attached to the body 4 of the augmented reality device 2 with the optical tracking system 18 comprised in the surgical navigation system 100. The position and orientation of the optical tracking device 8 in the reference coordinate system 42 can be described by a fourth transformation 48. A predetermined spatial relationship between the optical tracking device 8 and the location coordinate system 47 defined by the reference point of the augmented reality device 2, which predetermined spatial relationship is described by a fifth transformation 50, can then be used to determine the position and orientation of the augmented reality device 2 in the reference coordinate system 42. In other words, the position and orientation of the augmented reality device 2 in the reference coordinate system 42 can be determined using the localization system 16 comprised in the surgical navigation system 100.

Secondly, the position and orientation of the augmented reality device 2 in the reference coordinate system 42 can be determined based on the first transformation 38 and the third transformation 46. In other words, the position and orientation of the location coordinate system 47 defined by the reference point of the augmented reality device 2 can be determined in the reference coordinate system 42 using the internal tracking system 12 comprised in the augmented reality device 2 and using the first registration data.

A sixth transformation 52 which describes a position and orientation of the eye 14 of the user with respect to the location coordinate system 47 defined by the reference point of the augmented reality device 2 may be used in order to determine a viewing direction of the user. The sixth transformation may also be used to move the reference point of the augmented reality device 2, which describes an intended position of the eye 14, to the position of the eye 14. In this case, the fifth transformation 50 and the third transformation 46 are adjusted such that the sixth transformation 52 becomes essentially zero. This enables a compensation of an offset between the position of the eye 14 of the user and the intended position of the eye 14 defined by the reference point.

A seventh transformation 54 describes a position and orientation of the visual representation 34 of the reference object 24 in the coordinate system 40 of the augmented reality device 2. As indicated in FIG. 2, only the part 36 may be displayed to the user. In this case, the seventh transformation 54 may describe a position and orientation of part 36 in the coordinate system 40 of the augmented reality device 2. A first viewing direction 56 of the user is indicated in FIG. 2 by a dashed line and may be determined based on at least the sixth transformation 52. Another dashed line denoted by reference numeral 58 corresponds to a direction with reference to the eye 14, in which direction the visual representation 34 is displayed on the display system 6. This direction corresponds to a second viewing direction 58 which can be determined based on at least the sixth transformation 52.

The first transformation 38 is calibrated based on user interaction (i.e., user input) driven by a discrepancy between the reference object 24 and the visual representation 34 thereof. In the following, individual steps of this method are described in detail.

One or more verification features attached to the reference object 24, for example one or more optical markers 28, are used to both verify and calibrate the first transformation 38. Such verification features are particularly suitable if they can easily be recognized by the user from many perspectives and matched to a virtual representation of such feature. The optical markers 28 are detectable by the optical tracking system 18. At least two of the markers 28 may be optically indistinguishable from one another by the optical tracking system 18. In one variant, the optical markers 28 are arranged such that all markers can be detected at the same time by the optical tracking system 18. A distinction can be made between the individual optical markers 28 by the localization system 16 in case a non-symmetrical arrangement of the optical markers 28 is used. The optical markers 28 may be passive optical markers having a spherical form. This enables a reliable detection of the optical markers 28 from a plurality of viewing angles.

The verification features, i.e., the optical markers 28, must be rigidly attached to the reference object 24 for the duration of use. The verification features could be permanently attached to the reference object 24 or dynamically attached for the duration of use. Such dynamic attachment can be reproducible so that a positional relationship between the feature and the reference object 24 is known. Alternatively, the attachment is non-reproducible so that a positional relationship between the feature and the reference object 24 needs to be intra-operatively determined, e.g. by touching divots which represent the feature with a pointer tracked by the optical tracking system 18.

The most relevant examples of such verification features are: passive navigation marker spheres; active light-emitting diode, LED, elements; divots, corners or other protruding features of the reference object 24 or the body 26 and color markings on the reference object 24 or the body 26. As verification features, other objects may be used. For example, a position of a tip of a surgical instrument may be used as a verification feature or a nose of a patient. Also in these cases, the visual representation 34 of the verification feature needs to be available to be displayed by the augmented reality device.

To verify accuracy of the overlaid visual representation 34 with respect to the reference object 24, the surgical navigation system 100 is configured to display on the display system 6 the visual representation 34 of the verification feature in the augmented reality device 2 at a certain position. This certain position is described by the seventh transformation 54 with reference to the coordinate system 40 of the augmented reality device. Of course, additional transformations (i.e., the sixth transformation 52) may be used to determine the certain position. In one variant, additional information comprised in the viewing direction data or in the selection viewing direction data is used to determine the certain position. For example, a field of view of the user using the augmented reality device 2 or a distance between the eye 14 and the display system 6 may be taken into account. Note that in the example shown in FIG. 2, the visual representation 34 of the verification feature corresponds to part 36.

Based on the viewing direction data which describes the at least one first viewing direction 56 of the user, and based on the second registration data describing the second transformation 44, the first viewing direction 56 of the user with respect to the reference object 24 can be determined. In other words, it can be determined from which angle the user is looking at reference object 24 based on the first viewing direction 56 and based on the second transformation 44. This information is then used to determine the visualization data describing the visual representation 34.

The step of obtaining the viewing direction data may comprise obtaining at least one position and/or orientation of the augmented reality device 2. The at least one position and/or orientation of the augmented reality device 2 may be described in the reference coordinate system 42 by the viewing direction data. For example, in case the augmented reality device 2 is not able to track a position of the eye 14 of the user and thus not able to determine the sixth transformation 52, the first viewing direction 56 may be determined based on the fourth transformation 48 and the fifth transformation 50 and based on the sixth transformation 52 being a predetermined transformation. In other words, the first viewing direction 56 can be determined based on the tracking of the optical tracking device 8 attached to the body 4 of the augmented reality device 2, based on the known spatial relationship between the optical tracking device 8 and the reference point of the augmented reality device 2 described by the fifth transformation 50, and based on a predetermined spatial relationship between the reference point and the first viewing direction 56 described by the sixth transformation 52.

Alternatively, the at least one position and/or orientation of the augmented reality device 2 may be described in the coordinate system 40 of the augmented reality device 2 by the viewing direction data. For example, in case the augmented reality device 2 cannot be tracked by the tracking system 18, the position and/or orientation of the augmented reality device can be determined by the internal tracking system 12. The internal tracking system 12 may determine the third transformation 46 to describe the position and orientation of the reference point of the augmented reality device 2 in the coordinate system 40 of the augmented reality device 2.

In one variant, the step of obtaining the viewing direction data comprises obtaining at least one position and/or orientation of at least a part of the eye 14 of the user using the augmented reality device 2. This position and/or orientation are described by the sixth transformation 52. The position and/or orientation of at least the part of eye 14 of the user may be described in the location coordinate system 47 or in the coordinate system 40 of the augmented reality device 2. The first viewing direction 56 of the user can then be determined in the reference coordinate system 42 based on the fourth transformation 48, the fifth transformation 50 and the sixth transformation 52. In other words, the first viewing direction 56 of the user can be determined based on the tracking of the optical tracking device 8 attached to the body 4 of the augmented reality device 2, based on the known spatial relationship between the optical tracking device 8 and the reference point on the augmented reality device 2 described by the fifth transformation 50, and based on the tracking of a position of the eye 14 as described by the sixth transformation 52. Of course, the first viewing direction can be described in any one of the given coordinate systems. To determine the first viewing direction in another coordinate system, the transformations explained above are used. In addition, as noted above, the first viewing direction 56 of the user can also be determined based on a tracking of the augmented reality device 2 by the internal tracking system 12 instead of a tracking by the tracking system 18.

The first viewing direction 56 and the second viewing direction 58 can each be described by at least one ray and/or line associated with the reference coordinate system 42. The at least one ray and/or line may either be described in the reference coordinate system 42 or transformable into the reference coordinate system 42 by a known transformation, for example one of the transformations noted above. As indicated by dotted line 56 in FIG. 2, the first viewing direction may correspond to a line of sight originating at the eye 14 and pointing to the reference object 24. The second viewing direction 58 may correspond to a line of sight originating at the eye 14 and pointing to the visual representation 34.

The visual representation 34 of the reference object 24 can be determined based on the determined first viewing direction 56 and based on the reference object data. In particular, the reference object data describes geometric properties of the reference object 24 and may comprise a three-dimensional model of the reference object 24 which enables a determination of the visual representation 34 from the first viewing direction 56.

The visual representation 34 allows the user to see discrepancies between the visual representation 34 of a verification feature and the verification feature as such, for example between the visual representation 34 of a part of the reference object 24 and the part of the reference object 24. The user's vision of relevant surgical anatomy is not be occluded by the visual representation 34. Also, occluding relevant parts of the verification feature is avoided and ambient colors, lights and placement of objects in the operation room, OR, can be considered. Examples of a suitable visual representation 34 comprise: at least one outline of the verification feature (i.e., the marker 28), potentially based on the current perspective defined by the first viewing direction 56 or the second viewing direction 58; cross hairs for centering on the verification feature; and outsets or insets so that an alignment between the visual representation 34 of the reference object 24 to be displayed by the augmented reality device 2 and the reference object 24 is achieved by aligning the verification feature's outline with a contour shown in parallel either outside or inside the verification feature. The transparency of the visual representation 34 should be set to a medium value to optimize for both visibility of the visual representation 34 and the verification feature in general. The color of the visual representation 34 should be set to be complementary or contrasting to the verification feature's color and a most likely background object's color. Sensors comprised in the augmented reality device 2, for example a camera comprised in internal tracking system 12, might be used to detect what an appropriate color for the visual representation 34 should be. The visual representation 34 can be shown always or selectively based on user input or interaction which activates verification of the first transformation 38.

Such verification activating user input might be a positioning of the user's gaze or a system representation of the user's gaze such as a so-called gaze cursor on or near the verification feature or the visual representation 34 thereof. A further example of verification activating user input are a voice command such as "Start verification" and a gesture such as an air tap, pinch, drag, etc. another example of verification activating user interaction is an execution of a workflow as part of which the interaction is integrated.

The visual representation 34 can be deactivated based on user input or interaction which deactivates verification of the first transformation 38. An example of verification deactivating user interaction is a moving of the user's gaze or a system representation of the user's gaze such as the gaze cursor away a predefined distance or at a particular speed from the visual representation 34. Another example of verification deactivating user interaction is a holding of the user's gaze or a system representation of the user's gaze on the visual representation 34. Further examples of verification deactivating user input are a voice command such as "Stop verification" and a gesture such as an air tap, pinch, drag, etc. A further example of a verification deactivating user interaction is an execution of a workflow as part of which the interaction is triggered or a timer based interaction, such as a time out after a predetermined number of seconds.

In some embodiments a verification confirmation step may be performed after determining the calibrated first registration data describing the calibrated transformation. In particular, in some cases it is advantageous to ensure that the surgeon has accepted the accuracy of the calibrated transformation and only provide the overlaid visual representation 34 of the reference object 24 in case the user has explicitly confirmed the verification interaction.

For example, the available verification features are easily recognizable by the user on the reference object 24. In one embodiment, an indication of available verification features is displayed by display system 6 of the augmented reality device 2 when the user is looking at a verification feature on the reference object 24 or when the system representation of the gaze moves over the verification feature.

If many verification features exist, for example four optical markers 28 on reference object 24, a selection mechanism can be provided which enables one, all or several verification features and their visual representation 34, e.g., when holding the gaze or the system's representation of the gaze over the displayed visual representation 34. In other words, selection data might be obtained which describes a selection of a part of the reference object 24, the selection data being determined based on a selection of the user. For example, the selection viewing direction data is obtained which describes the at least one second viewing direction 58 of the user in the reference coordinate system 42. The obtaining of the selection viewing direction data may comprise obtaining at least one position and/or orientation of at least a part of the eye 14 of the user using the augmented reality device 2. In one variant, obtaining the selection viewing direction data comprises obtaining at least one position and/or orientation of the augmented reality device 2 in the reference coordinate system 42. The viewing direction of the user can be determined as described above with respect to the viewing direction data. That is, the second viewing direction 58 can be determined in a similar manner as described above for the first viewing direction 56. Subsequently, a selection of a part of reference object 24 may be determined based on the second viewing direction 58. In particular, a part 36 of the visual representation 34 of the reference object 24 displayed by the display system 6 of the augmented reality device 2 in the reference coordinate system 42 at a position corresponding to the second viewing direction 58 described by the selection viewing direction data is determined as the selected part.

In case a deviation between the position at which visual representation 34 is displayed and a position at which reference object 24 is situated is present, a calibration of the first transformation 38 can be performed. The calibration method may be started based on the aforementioned verification, but may also be started independently.

Trigger data may be determined based on an input of the user. The trigger data describes a trigger signal which starts the calibration method. The trigger data may be determined in case the gaze cursor is focused on a desired position of the visual representation 34 of the verification feature. Other types of user input are possible. In the case of the outline visualization of the visual representation 34 the user could for instance move the outline using the gaze cursor so that the outline of the visual representation 34 matches a contour of the verification feature. In case of the crosshair visualization the user could position the gaze cursor on the center of the verification feature. Virtual buttons could be used to move the visual representation of the verification feature into the desired position. Relative head movement may be used to move the visual representation of the verification feature into the desired position. For example, when the user wants to indicate that the visual representation 34 should be moved to the right side, the user may move his or her head to the right relative to the current perspective of looking at the verification feature. The calibration method would then adjust the first transformation 38 so that in addition to the perspective change of moving the head, the visual representation 34 would also be moved an additional amount to the right. Voice commands may be used to move the visual representation 34 to the desired position. For example, by giving the voice command "up" the visual representation 34 can be moved up relative to the current perspective of looking at the verification feature such as the marker 28.

In general the calibration of the first transformation 38 can be described by either translational operations of the first transformation 38 or using an intermediate step of calculating the sixth transformation 52 and updating the first transformation 38 based on the sixth transformation 52. The calibrated first registration data can be determined by determining an internal transformation 59 between a position at which the visual representation 34 of the reference object 24 is to be displayed and the at least one first viewing direction 56. The internal transformation 59 can then be applied to the first transformation 38 or the first transformation 38 can be applied to the internal transformation 59.

Figure 3:
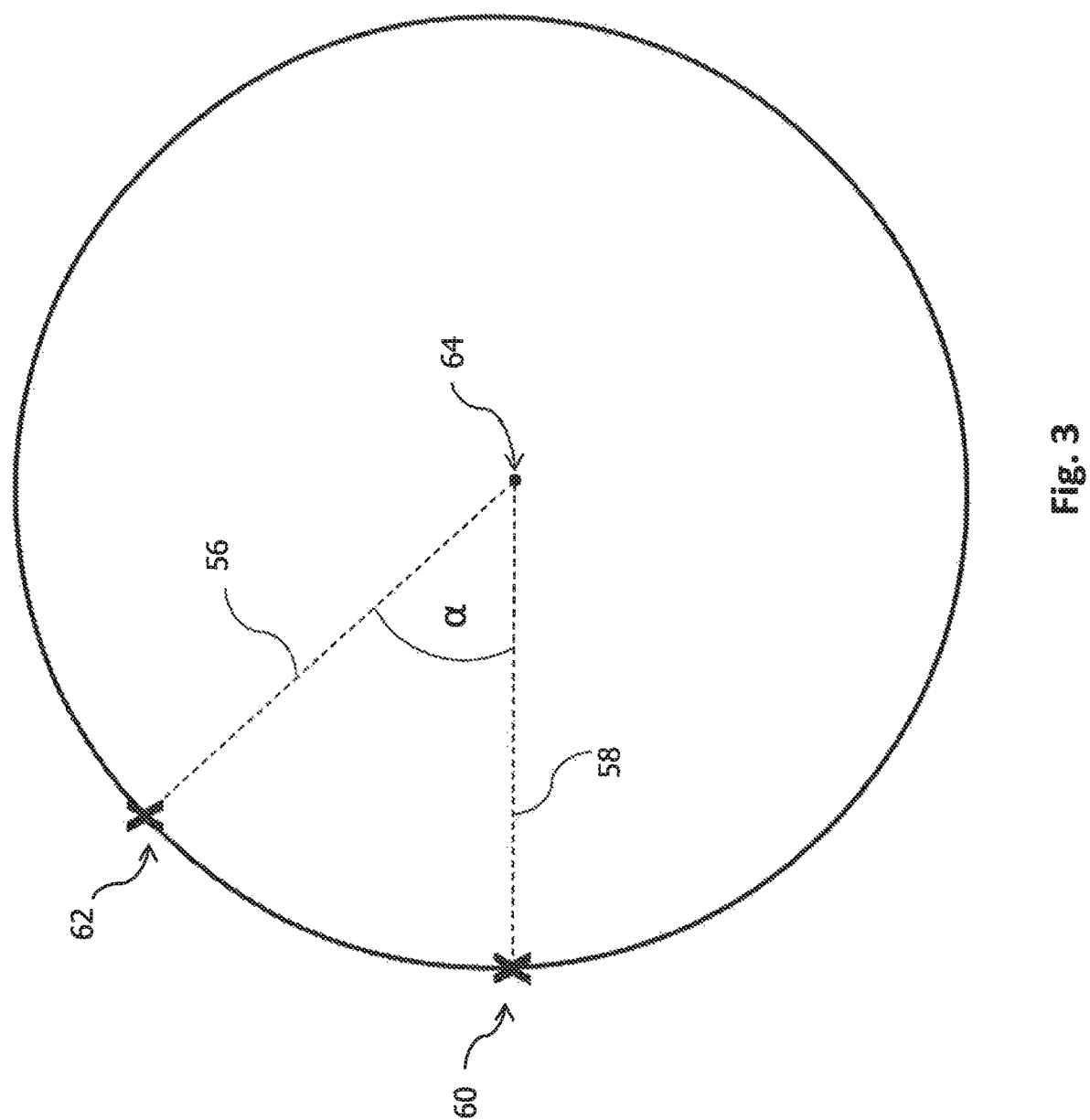
FIG. 3 shows an example of determining an internal transformation.

FIG. 3 shows an example of determining an internal transformation 59. A first position 60 at which the visual representation 34 of the reference object 24 is displayed is shifted to a second position 62 at which the reference object 24 is situated. In the shown example, both positions 60 and 62 can be described in the reference coordinate system 42. The first position 60 is shifted to the second position 62 by applying a rotational transformation. In particular, the first position 60 is rotationally shifted by angle α around rotation point 64. Rotation point 64 corresponds to the reference point of the augmented reality device 2. Alternatively, it may correspond to a position of the eye 14 of the user of the augmented reality device 2. In other words, the distance between the rotation point 64 and the first position 60 is equal to the distance between the rotation point 64 and the second position 62. First position 60 and rotation point 64 define a sphere with a radius corresponding to the distance between the first position 60 and rotation point 64 and the center of the sphere defined by rotation point 64. The first viewing direction 56 intersects rotation point 64 and intersects the sphere at second position 62. The internal transformation 59 corresponds to the rotational shift between the first position 60 and the second position 62. Note that the first position 60 may correspond to a position at which a part 36 of the visual representation 34 displayed by the augmented reality device 2 is displayed (i.e., where a virtual object representing the part of the reference object 24 is to be situated by the visual representation 34) and the second position 62 may correspond to a position at which the part of the reference object 24 is situated. That is, the first position 60 corresponds to a position of a visualization of an object, whereas the second position 62 corresponds to a position of the object in the real world.

The calibration may be performed several times with different first viewing directions. Alternatively or additionally, several first viewing directions may be described by the viewing direction data and the calibration is performed based on the several first viewing directions. Several different viewing directions may be used to determine an a look-at point, for example using an optimization algorithm minimizing the distance between each viewing direction and the look-at point. The look-at point may then be used as the second position 62. In this case, no rotation point is necessary. Instead, the first position 60 may be shifted to the second position 62 using a translational and/or rotational transformation which is then defined as the internal transformation 59.

Once the user has performed a calibration update interaction, the visual representation 34 is updated based on the calibrated first registration data so that the accuracy of the attained calibrated transformation can be verified. In general this might be the same type of visualization as shown during the verification interaction, but it also might differ therefrom.

As with the verification described above, an easy way to abort, repeat and confirm the calibration method may be provided. The aborting may be based on user input. To abort the calibration method, a user may move his gaze or a system representation of the user's gaze in a particular fashion. For example, the gaze cursor may be moved away from the visual representation 34 a predefined distance, moved away at a particular minimum speed from the visual representation 34 or moved in a particular direction indicated by an appropriate visualization (e.g. moving towards a red half semicircle being shown on the left from the visual representation 34), or moved in a particular direction derived from considering the position of the surgical site, e.g. moving away from the situs. Alternatively, the user may hold his gaze or a system representation of the user's gaze still on a virtual screen element such as a button labeled with an appropriate phrase such as "Cancel", "Abort" etc. or an appropriate symbol/icon such as a red "X". The user may hold his gaze or a system representation of the user's gaze still on the visual representation 34 or part thereof (unless used to confirm the calibration) in order to abort the calibration method. To abort, a voice command such as "Stop calibration" or a gesture such as an air tap, pinch, drag, etc. may be used. In another variant, the calibration method is aborted in case a workflow is executed as part of which the calibration method is to be aborted. Also, a timer-based interaction, such as a time out after a number of seconds or a head movement, such as shaking the head may be used as user interaction (i.e., user input) aborting the calibration method.

The calibration may be confirmed based on user interaction or input. Such user interaction or user input may comprise moving the user's gaze or a system representation of the user's gaze, for example moving the gaze cursor away from the visual representation 34 a predefined distance, moving the gaze cursor away at a particular maximum speed from the visual representation 34, moving in a particular direction indicated by an appropriate visualization (e.g. moving towards a green half semicircle being shown on the right from the visual representation 34) or moving in a particular direction derived from considering the position of the surgical site, e.g. moving towards the situs. Alternatively, in order to confirm the determined first transformation 38, a user may hold his gaze or a system representation of the user's gaze still on a virtual screen element such as a button labeled with an appropriate phrase such as "OK", "Confirm", etc. or an appropriate symbol/icon such as a green checkmark. The user may also hold his gaze or a system representation of the user's gaze still on the visual representation 34 or part thereof (e.g., part 36) to confirm the calibrated transformation. Alternatively, a voice command such as "Confirm calibration" or a gesture such as an air tap, pinch, drag, etc. may be used as user input to confirm the calibrated transformation 38. The confirmation may be based on an execution of a workflow as part of which the calibrated transformation is confirmed. As the user interaction or input to confirm the calibrated transformation, a timer-based interaction, such as a time out after a number of seconds or a head movement, such as nodding, may be used.

The calibration method may be repeated. For example, the method is repeated with the same visual representation 34 and/or with different first viewing directions. The same part 36 of the visual representation 34 of the reference object 24 may be used in a consecutive execution of the calibration method. Alternatively, another part 36 of the visual representation 34 of the reference object 24 may be used in a consecutive execution of the calibration method. The calibration method may be repeated from another perspective, i.e., using a different first viewing direction.

Appropriate sounds may be output from the surgical navigation system 100, for example from a speaker comprised in the augmented reality device 2, to signal acceptance and rejection of any user action, completion or abortion of a computation or the calibration method.

In case the surgical navigation system 100 is using two or more reference objects 24 concurrently, it is plausible to consider using the reference object 24 for the calibration which has the most prominent verification features, for example markers 28.

Both optical tracking devices which are rigidly fixed to the patient anatomy (patient trackers) and moveable optical tracking devices can be considered as the reference object 24 to be used for calibrating the first transformation 38. Rigidly connected optical tracking devices are more likely to be relevant as they will be appropriately positioned, but also moveable optical tracking devices might be preferred by the user for verification and calibration. Semi-rigidly fixed optical tracking devices e.g. on articulated arms of a surgical robotic device comprised in the surgical navigation system 100 might also be used as the reference object 24.

Time synchronization between a system clock comprised in the augmented reality device 2 and a system clock comprised in the localization system 16 should be provided, for instance by correlating movement trajectories obtained by the localization system and the internal tracking system 12 comprised in the augmented reality device 2, respectively. Alternatively, a network-based clock synchronization might be applied, wherein the augmented reality device 2 and the localization system 16 are connected to the network. In case the system clocks comprised in the augmented reality device 2 and the localization system 16 are synchronized, tracking information from both components can be integrated reliably into a common frame of reference, for example the reference coordinate system 42.

Figure 4:
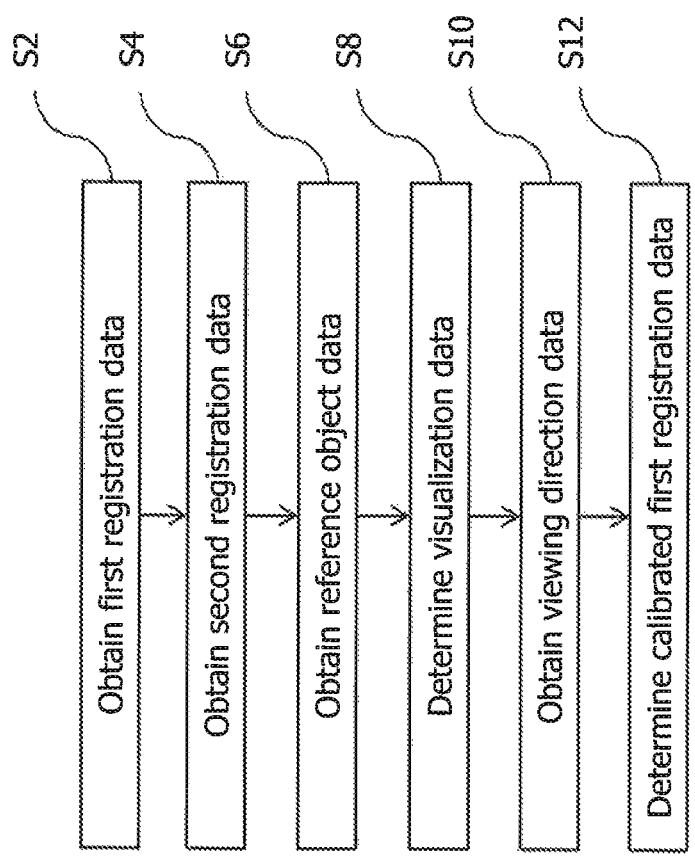
FIG. 4 shows a method embodiment according to the present disclosure.

FIG. 4 shows a flow diagram that illustrates a method embodiment according to the present disclosure. The method may be executed by the surgical navigation system 100, for example by processor 30.

The method comprises a step S2 of obtaining the first registration data. The first registration data describes the first transformation 38 between the coordinate system 40 of the augmented reality device 2 and the reference coordinate system 42 of the surgical navigation system 100. The method further comprises a step S4 of obtaining the second registration data. The second registration data describes the second transformation 44 between the coordinate system of the reference object 24 and the reference coordinate system 42. The reference object 24 is for example an optical tracking device comprising the body 26 and the optical markers 28 detectable by optical tracking system 18 of the surgical navigation system 100.

The method also comprises a step S6 of obtaining the reference object data. The reference object data describes the geometric properties of the reference object 24, for example a three-dimensional model of the optical tracking device. The method also comprises a step S8 of determining the visualization data. The visualization data is determined based on the first registration data, the second registration data and reference object data. The visualization data describes the visual representation 34 of the reference object 24 to be displayed by the augmented reality device 2. The visualization data describes a virtual representation of the reference object 24 which is to be displayed in an overlaid manner by the augmented reality device 2 over the reference object 24.

The method further comprises step S10 of obtaining the viewing direction data. The viewing direction data describes the at least one first viewing direction 56 of the user using the augmented reality device 2. The at least one first viewing direction 56 is associated with the reference coordinate system 42. In step S12 comprised in the method, the calibrated first registration data is determined. The calibrated first registration data is determined based on the first registration data and the viewing direction data. The calibrated first registration data describes the calibrated first transformation 38, which is a transformation between the coordinate system 40 of the augmented reality device 2 and the reference coordinate system 42.

It will be evident that the method illustrated in the flow diagram of FIG. 4 can comprise further steps as generally described herein.

A program is provided comprising instructions which, when executed by processor 30, cause the processor 30 to perform the method described herein. The program is for example stored in data storage 32. The program may be transmitted via a data stream.

In summary, the problem of how to verify the accuracy of the first transformation 38 between the augmented reality device 2 and the reference coordinate system 42 of the navigation system 100 (and potentially calibrate the first transformation 38 in case of a detected offset) is addressed with the technique presented herein. The technique presented herein is particularly relevant for HMDs which do not provide a tracking of the eye 14 of the user wearing the augmented reality device 2, augmented reality devices 2 which are not equipped with a high accuracy tracking system or in case the tracking system 18 cannot always accurately track the position or orientation of the augmented reality device 2. The tracking device which is attached to the patient for surgical navigation may, in addition to tracking the position of the patient, by used as the reference object 24 for verification and calibration of the first transformation 38.

Surgeons are sterile and cannot interact with any non-sterile object (including the augmented reality device 2). Moreover, surgeons are often constrained in their movements (e.g., they should not raise their hands too high). Also, space is constrained in the operation room and near the situs. The technique presented herein enables verification and calibration of the first transformation 38 despite these constraints.

In addition, the verification and calibration will likely need to be performed prior to each safety critical action. The technique presented herein is quick to perform, thereby addressing also this issue.

The technique presented herein also is safe for the user and patient, in particular regarding the use of sharp objects and the risk of dropping objects into the surgical site. In addition, the surgeon usually has surgical instruments in both hands in situations when he needs accuracy the most. The technique presented herein can be performed hands-free and is thus safe for the user and patient.

Importantly, the technique presented herein is effective to attain the desired accuracies. As such, the surgical results can be improved.

While the present disclosure has been described with reference to exemplary embodiments, it will be appreciated that the present disclosure can be modified in many ways without departing from the scope of the invention as defined by the appended claims.

The invention claimed is:

1. A method of calibrating a registration of an augmented reality device comprised in a surgical navigation system, the method comprising:
   obtaining first registration data describing a first transformation between a coordinate system of the augmented reality device and a reference coordinate system of the surgical navigation system;
   obtaining second registration data describing a second transformation between a coordinate system of a reference object and the reference coordinate system of the surgical navigation system;
   obtaining reference object data describing geometric properties of the reference object;
   determining visualization data based on the first registration data, the second registration data and the reference object data, the visualization data describing a visual representation of the reference object to be displayed by the augmented reality device;

obtaining viewing direction data describing at least one first viewing direction of a user using the augmented reality device, the at least one first viewing direction being associated with the reference coordinate system of the surgical navigation system; and determining calibrated first registration data based on the first registration data and the viewing direction data, the calibrated first registration data describing a calibrated transformation between the coordinate system of the augmented reality device and the reference coordinate system, wherein the step of determining calibrated first registration data comprises determining an internal transformation between a position at which the visual representation of the reference object is to be displayed and the at least one first viewing direction.

2. The method of claim 1, further comprising a step of obtaining trigger data describing a trigger signal to execute at least one of the obtaining of the first registration data, the obtaining of the second registration data, the determining of the visualization data, the obtaining of the viewing direction data and the determining of the calibrated first registration data, the trigger data being determined based on input of a user using the augmented reality device.

3. The method of claim 1, further comprising a step of obtaining selection data describing a selection of a part of the reference object, the selection data being determined based on a selection of the user.

4. The method of claim 3, wherein the step of obtaining selection data comprises:
obtaining selection viewing direction data describing at least one second viewing direction of the user, the at least one second viewing direction being associated with the reference coordinate system;
determining the selection of the part of the reference object by determining a part of the reference object which part's visual representation is to be displayed by the augmented reality device at a position corresponding to the at least one second viewing direction described by the selection viewing direction data.

5. The method of claim 4, wherein the at least one second viewing direction of the user is compared with a reference viewing direction and, if the obtained at least one second viewing direction of the user corresponds to the reference viewing direction within a given tolerance limit, the part of the reference object which lies in the reference viewing direction is selected.

6. The method of claim 4, wherein
at least one of the at least one first viewing direction and the at least one second viewing direction is described by at least one ray and/or a line representing a line of sight of an eye of the user using the augmented reality device.

7. The method of claim 1, wherein
the reference object includes markers detectable by a tracking system comprised in the surgical navigation system.

8. The method of claim 7, wherein
at least two of the markers are indistinguishable from one another by the tracking system.

9. The method of claim 1, wherein
at least one of the step of obtaining viewing direction data and the step of obtaining selection viewing direction data comprises obtaining at least one position and/or orientation of the augmented reality device.

10. The method of claim 1, wherein
at least one of the step of obtaining viewing direction data and the step of obtaining selection viewing direction data comprises obtaining at least one position and/or orientation of at least a part of an eye of the user using the augmented reality device.

11. The method of claim 1, wherein
the step of determining calibrated first registration data comprises one of applying the internal transformation to the first transformation and applying the first transformation to the internal transformation.

12. The method of claim 1, wherein the internal transformation is a rotational transformation.

13. The method of claim 12, wherein the rotational transformation describes a rotation around a rotation point corresponding to a position of an eye of the user using the augmented reality device.

14. The method of claim 1, wherein the internal transformation describes a transformation between the position at which the visual representation is to be displayed and a focus point or a look-at point of the user using the augmented reality device.

15. The method of claim 1, wherein the viewing direction data comprises information about at least one of:
a field of view of the user; and
a distance between an eye of the user and a display of the augmented reality device.

16. The method of claim 1, wherein the viewing direction data describes a plurality of lines and/or rays having a common intersection point.

17. The method of claim 16, wherein the common intersection point corresponds to a focus point of the user or to a look-at position associated with the reference coordinate system.

18. An apparatus for calibrating a registration of an augmented reality device comprised in a surgical navigation system, the apparatus configured to:
obtain first registration data describing a first transformation between a coordinate system of the augmented reality device and a reference coordinate system of the surgical navigation system;
obtain second registration data describing a second transformation between a coordinate system of a reference object and the reference coordinate system of the surgical navigation system;
obtain reference object data describing geometric properties of the reference object;
determine visualization data based on the first registration data, the second registration data and the reference object data, the visualization data describing a visual representation of the reference object to be displayed by the augmented reality device;
obtain viewing direction data describing at least one first viewing direction of a user using the augmented reality device, the at least one first viewing direction being associated with the reference coordinate system of the surgical navigation system; and
determine calibrated first registration data based on the first registration data and the viewing direction data, the calibrated first registration data describing a calibrated transformation, which is a transformation between the coordinate system of the augmented reality device and the reference coordinate system, wherein determining calibrated first registration data comprises determining an internal transformation between a position at which the visual representation of the reference object is to be displayed and the at least one first viewing direction.

19. A method of calibrating a registration of an augmented reality device comprised in a surgical navigation system, the method comprising:
- obtaining first registration data describing a first transformation between a coordinate system of the augmented reality device and a reference coordinate system of the surgical navigation system;
- obtaining second registration data describing a second transformation between a coordinate system of a reference object and the reference coordinate system of the surgical navigation system;
- obtaining reference object data describing geometric properties of the reference object;
- determining visualization data based on the first registration data, the second registration data and the reference object data, the visualization data describing a visual representation of the reference object to be displayed by the augmented reality device;
- obtaining viewing direction data describing at least one first viewing direction of a user using the augmented reality device, the at least one first viewing direction being associated with the reference coordinate system of the surgical navigation system;
- determining calibrated first registration data based on the first registration data and the viewing direction data, the calibrated first registration data describing a calibrated transformation between the coordinate system of the augmented reality device and the reference coordinate system; and
- obtaining selection data describing a selection of a part of the reference object, the selection data being determined based on a selection of the user, wherein the step of obtaining selection data comprises:
- obtaining selection viewing direction data describing at least one second viewing direction of the user, the at least one second viewing direction being associated with the reference coordinate system; and
- determining the selection of the part of the reference object by determining a part of the reference object which part's visual representation is to be displayed by the augmented reality device at a position corresponding to the at least one second viewing direction described by the selection viewing direction data.

20. The method of claim 19, wherein the at least one second viewing direction of the user is compared with a reference viewing direction and, if the obtained at least one second viewing direction of the user corresponds to the reference viewing direction within a given tolerance limit, the part of the reference object which lies in the reference viewing direction is selected.

* * * * *